United States Patent [19]

Greene

[11] Patent Number: 4,517,301

[45] Date of Patent: May 14, 1985

[54] KETONE CONTROL TEST COMPOSITION, METHOD AND TEST DEVICE

[75] Inventor: Carmine M. Greene, Mishawaka, Ind.

[73] Assignee: Miles Laboratories, Inc., Elkhart, Ind.

[21] Appl. No.: 447,321

[22] Filed: Dec. 6, 1982

[51] Int. Cl.$^3$ .............................................. G01N 33/48
[52] U.S. Cl. ..................................... 436/14; 436/128; 436/169; 422/56
[58] Field of Search ................. 436/14, 128, 169, 170; 422/56, 57

[56] References Cited

U.S. PATENT DOCUMENTS

| | | | |
|---|---|---|---|
| 2,509,140 | 5/1950 | Free | 252/408.1 |
| 4,071,317 | 1/1978 | Lam | 436/169 X |
| 4,193,766 | 3/1980 | Daunora et al. | 436/14 |
| 4,298,498 | 11/1981 | Rehner et al. | 436/14 X |
| 4,372,747 | 2/1983 | Gabbay et al. | 252/408.1 X |

FOREIGN PATENT DOCUMENTS 496345  1/1938  United Kingdom ................. 422/57

*Primary Examiner*—Teddy S. Gron
*Assistant Examiner*—Catherine S. Kilby
*Attorney, Agent, or Firm*—Roger N. Coe

[57] ABSTRACT

A composition, device and method for preparing a ketone control solution are disclosed. The composition comprises dimethylformamide and a Group I, II or III metal salt of a β-keto acid ester. The salt has the structure

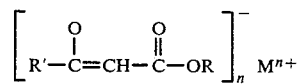

in which R is lower alkyl of 1 to 6 carbon atoms, R' is an aliphatic or cyclic group having 1 to about 7 carbon atoms, M is a Group I, II or III metal ion and n is 1, 2 or 3. A carrier matrix incorporated with the composition can be affixed to a support member to form the device. Preferably, a hydrolyzing agent is included on the device in the same or another carrier matrix. The method for preparing the control solution comprises contacting a predetermined volume of an aqueous solution with the device for a predetermined time.

18 Claims, No Drawings

KETONE CONTROL TEST COMPOSITION, METHOD AND TEST DEVICE

BACKGROUND OF THE INVENTION

1. Field of the Invention

This invention relates generally to the analysis of an analyte in a solution and particularly to the preparation of a control solution for analytical tests for the presence of ketone bodies, for example, in biological fluids.

Ketone bodies are the common designation for the group of compounds including acetoacetic acid, $\beta$-hydroxybutyric acid and acetone. Acetoacetic acid is a normal end product of fatty acid oxidation in the liver, and is also produced, to a very limited extent, by the oxidative breakdown of leucine, alanine and tyrosine. $\beta$-hydroxybutyric acid is formed from acetoacetic acid by reversible reduction. Acetone is produced through nonreversible decarboxylation of acetoacetic acid:

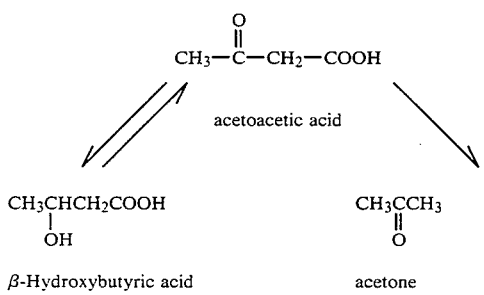

Abnormally high amounts of ketone bodies in urine or blood are referred to as ketonuria and ketonemia, respectively. These abnormalities can occur as a result of such diverse conditions as diabetes mellitus and starvation. An example of the importance of monitoring the level of ketone bodies in such biological fluids is that detection of ketonuria in the diabetic may indicate the need for a change in insulin dosage (or other disease management procedure).

2. Background Art

Analytical procedures for determining the presence of sample constituents, whether gravimetric, volumetric, spectrophotometric or the like, should be evaluated periodically for reliability of results. Unless the reliability of such procedures is assessed, any data developed from them is meaningless. Therefore, devising and maintaining an appropriate analytical procedure must necessarily include quality control measures, for example, evaluation of experimental error produced by the procedure, or assessment of the training and efficiency of the technologist performing it. In other words, some means of predicting the dependability of the data produced by a person conducting the procedure is crucial to its successful use. In addition, it is desirable to have such controls available for training purposes.

The most efficacious and direct way to evaluate parameters such as reproducibility of results, sensitivity and accuracy of an analytical procedure, and to aid the training of technologists in the procedure, is to subject the procedure to a test sample wherein the presence and/or concentration of the substance being determined, or one which simulates the analyte, is known. Such a test sample is termed a control, and data furnished by the procedure can thereby be compared with known data to reveal discrepancies.

Exemplary of known analytical control devices is CHEK-STIX®, a product marketed by the Ames Division of Miles Laboratories, Inc. It consists of various pads of bibulous carrier mounted on a strip of plastic, each pad being impregnated with one or more substances which, when dissolved in water, simulate pathological urine constituents. Accordingly, when a CHEK-STIX device is immersed in a premeasured volume of water for a predetermined time, a control solution results which simulates urine containing such metabolites as glucose, bilirubin, urobilinogen, ketone, occult blood, nitrite and protein. Such a control solution can, for example, be used to monitor the test devices known as N-MULTISTIX® and KETO-DIASTIX®, both dip-and-read analytical devices marketed by the Ames Division of Miles Laboratories, Inc.

Another example of a control device is embodied by the product TEK-CHEK®, also marketed by the Ames Division of Miles Laboratories, Inc. It comprises lyophilized urine containing natural and artificial additives to simulate both normal and pathological urine. In use, TEK-CHEK control device is added to a premeasured quantity of water to form the control solution.

The N-MULTISTIX and KETO-DIASTIX reagent test devices determine ketone bodies by the nitroprusside-ketone complexing phenomenon. When contacted with an aqueous ketone solution, the formation of a colored complex indicates the presence of a ketone; an estimate of the ketone concentration can be based on the intensity and hue of the color formed.

The aforedescribed TEK-CHEK control utilizes a pH indicator as a chemical substitute for ketone in lyophilized urine. The substitute is used because ketones are difficult to maintain in their natural state. However, while this chemical substitute is stable, its use in the control does not provide a positive test for ketones, but merely indicates the active presence of the base used in a ketone test.

U.S. Pat. No. 4,193,766, commonly assigned herewith, is directed to a device useful in the preparation of a ketone control solution. The device utilizes certain metal ion complexes of acetylacetone and its homologs as a substrate.

Many early ketone reagent tests were not specific for $\beta$-keto acids. Accordingly, compounds such as $\beta$-diketones or acetone were commonly used in controls for such tests, as these were known to be more stable, particularly under heat stress, than $\beta$-keto acids. U.S. Patent Application Ser. No. 324,779 (continuation of Ser. No. 90,926), commonly assigned herewith, discloses a device for preparing a ketone control solution wherein sodium enolate derivatives of $\beta$-keto esters are used. The device is, therefore, useful for the preparation of a control solution for ketone tests which are specific for $\beta$-keto acids.

SUMMARY OF THE INVENTION

The present invention involves the discovery of a significant advance in the art over all of the previously described ketone control compositions and devices. The instant invention provides a composition, a control test device including the composition, and a method for using the device for preparing a positive control test solution for a ketone test which is specific for $\beta$-keto acids. Compositions and control devices made in accordance with the invention have been found, surprisingly, to be advantageous over heretofore known controls for ketone tests, especially in providing enhanced long-term storage capability (shelf-life), and increased stability under heat stress conditions.

A composition according to the invention comprises dimethylformamide (DMF) and a Group I, II or III metal salt of a β-keto ester, for example, sodium methyl acetoacetate. Such ester salts can be represented by the general formula:

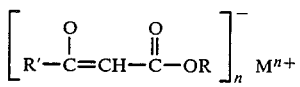

in which R is a lower alkyl group of 1 to 6 carbon atoms, R' is an aliphatic or cyclic group having 1 to about 7 carbon atoms, M is a Group I, II or III metal ion and n is 1, 2, or 3. A control device according to the invention comprises a carrier matrix which is incorporated with the composition and, preferably, affixed to a support member, such as a rigid or semirigid plastic strip, by means of double-sided tape or another suitable adhesive.

In one preferred embodiment, a control device of the invention can further comprise a hydrolyzing substance which is capable of converting the ester salt to the corresponding β-keto acid, and which is incorporated in the carrier matrix or in a second carrier matrix affixed to the support member. Such a hydrolyzing agent can be, and preferably is, a base such as a sodium or potassium hydroxide or carbonate, or mixtures thereof. The hydrolyzing base functions to increase the rate at which the ester salt is converted to free β-keto acid when the device is used to form a control solution.

A method for preparing a ketone control solution is also provided by the instant invention. The method comprises contacting a predetermined volume of an aqueous solution with the control device for a predetermined time. The control solution can then be used for determining the reactivity, and therefore the reliability, of a ketone test which is specific for β-keto acids, for example, either by visual or by spectrophotometric means. In addition, the control device can be used to prepare control solutions useful in the calibration of instruments such as spectrophotometers and the like.

DETAILED DESCRIPTION OF THE INVENTION

The focus of the instant invention is not only to provide a ketone control composition and control device which have the advantages of enhanced stability under heat stress conditions and prolonged storage, but also to provide such a composition and device which are easily reconstitutable in aqueous solution to provide β-keto acids, and, therefore, a positive control test solution for β-keto acid-specific ketone tests. This latter feature is accomplished by hydrolysis of the compounds in the composition to form such a control solution, and the invention has been found to enable a sufficient concentration of the β-keto acid to be produced in solution from the hydrolysis to be useful for providing a valid indication of the reactivity of a ketone test, and thus the reliability of the results therefrom. In use, the concentration range of acetoacetic acid in a control solution produced from a device made according to a preferred embodiment of the invention has been determined to be from about 10 to about 45 milligrams (mg) per deciliter (dl) of solution, a range effective as an optimum control solution for most β-keto acid-specific ketone tests.

Early experimental attempts to use compounds such as methyl acetoacetic acid alone in a ketone control composition were not highly successful due to the poor storage stability of such compositions, which usually lost significant reactivity, i.e., ability to undergo hydrolysis, after short periods of time. Moreover, some esters of acetoacetic acid were experimentally introduced into control compositions but were found not to be readily soluble in water, preventing rapid and efficient formation of control solutions therefrom. It has been discovered, however, that certain salts of β-keto esters are not only generally soluble in water and other aqueous solutions, and readily undergo hydrolysis to β-keto acids when placed into solution, but also, when combined with DMF, do not appear to lose significant reactivity, i.e., ability to hydrolyze substantially completely, even when stored for prolonged periods of time, under ambient or elevated temperatures. Salts of β-keto esters which are generally useful in the present invention can be represented by the structure

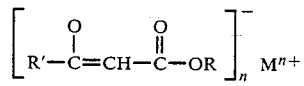

in which R is a lower alkyl group of 1 to 6 carbon atoms, R' is an aliphatic or cyclic group having 1 to about 7 carbon atoms, M is a Group I, II or III metal ion and n is 1, 2 or 3. Preferably, R and R' are methyl, and an especially preferred compound is sodium methyl acetoacetic acid (NaMeAA). M can also be such metals as, for example, Li, K, Mg, Ca, Sr, Ba, Al and others which are members of Groups I, II and III of the Periodic Table of the Elements.

It has been found necessary to formulate a control composition of the invention to include a nonaqueous solvent in order to solubilize the salt used and to prevent premature hydrolysis, and concomitant loss of reactivity, during the preparation and short-term storage of the composition. Many such solvents and solvent combinations were tested during experimental development of the invention to arrive at one optimum solvent for the useful salts of the esters. Only three of those tested demonstrated substantial ability to solubilize such salts: dimethyl formamide, ethylene diamine and a solution of 50 gram (g) % 2-methoxyethanol. However, DMF was ultimately chosen for use in the present invention because ethylene diamine was found to offer no apparent advantages over DMF and is caustic, whereas the 2-methoxyethanol composition exhibited a brown color. Because a colored control solution would interfere with a color-based determination of ketone reactivity, this latter solvent was determined to be unsuitable for the purposes of the present invention.

In a preferred embodiment, the control composition of the invention, comprising the salt of a β-keto ester and DMF, is incorporated into a suitable carrier matrix. The term "carrier matrix", as used herein, refers to any means suitable for containing a specified amount of the composition of ester salt and DMF, or in a preferred embodiment, these substances and a hydrolyzing substance. It can, therefore, comprise a wide range of materials. In fabrication of a control device of the invention, the carrier matrix is incorporated with a known amount of the composition, dried, and, when used, is immersed in a predetermined volume of an aqueous solution for a predetermined time and thereafter removed, leaving the ingredients behind in the solution.

The carrier matrix, accordingly, can comprise any substance capable of being incorporated with the ingredients. Thus, the matrix can take on many known forms, such as those utilized for reagent strips for solution analysis. For example, U.S. Pat. No. 3,846,247 teaches the use of felt, porous ceramic strips and woven or matted glass fibers. As substitutes for paper, U.S. Pat. No. 3,522,928 teaches the use of wood sticks, cloth, sponge material and argillaceous substance. The use of synthetic resin fleeces and glass fiber felts in place of paper is suggested in British Pat. No. 1,369,139. Another British Pat., No. 1,349,623, suggests the use of a light-permeable meshwork of thin filaments as a cover for an underlying paper matrix. This reference also suggests impregnating the paper with part of a reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513, wherein the concept of printing reagents onto a suitable carrier matrix is employed. U.S. Pat. No. 4,046,514 discloses the interweaving or knitting of filaments bearing reagents in a reactant system.

It is, therefore, to be appreciated that in producing control devices of the invention all such carrier matrix concepts can be employed, as can others. However, preferably the carrier matrix includes a bibulous material, such as filter paper, whereby a solution of the composition can impregnate the matrix. However, the matrix can also include a system which physically entraps any or all of these ingredients, such as polymeric microcapsules which rupture upon contact with an aqueous solution. For example, the hydrolyzing agent can be maintained separately within the same carrier matrix as the composition, without interaction therewith until contacted with a solution. The matrix can also comprise a system wherein the composition ingredients are homogeneously combined in a fluid or semifluid state, which later hardens or sets, thereby entrapping the ingredients.

The presently preferred method, however, is to impregnate a bibulous matrix, e.g., filter paper, with the composition, and, in a preferred embodiment, impregnate a second paper matrix with the hydrolyzing agent, followed by affixing of the impregnated matrices to a support member. The impregnation can be accomplished merely by dipping one piece of filter paper into the composition, and a second into the hydrolyzing agent, and drying.

Drying can be accomplished by any means which will not deleteriously affect the impregnated composition and hydrolyzing agent, usually by means of an air oven. In any event, the extent of drying should not be enough to drive off all of the DMF incorporated with the paper. The dried paper can thereafter but cut into a square measuring about 2/5 inch on a side, which is then mounted on one end of a support member, for example, a rigid or semi-rigid polystyrene film strip measuring about 3-4 inches long by 2/5 inch wide. Mounting of the paper on the strip can be accomplished through use of a double-faced adhesive tape, such as that commercially available from the 3M Co. as DOUBLE STICK ®.

The hydrolyzing agent, which in a preferred embodiment of the invention serves to accelerate the rate of hydrolysis of the $\beta$-keto ester salt to $\beta$-keto acid when the invention is used to form a control solution, can range widely. Examples of suitable hydrolyzing agents include bases such as sodium carbonate, potassium carbonate, sodium hydroxide and potassium hydroxide, and mixtures thereof, as well as mixtures of sodium bicarbonate and these substances. As used herein, "hydrolyzing agent" is intended to mean acids or bases of suitable strength to hydrolyze the ester salt, in solution. Some acids suitable for this purpose are the toluene sulfonic acids, benzene sulfonic acid, sulfosalicylic acid, the naphthalene disulfonic acids, and others.

The feature mainly determinative in selecting the hydrolyzing agent is the ultimate pH produced in solution. If a base is to be used, too low a pH will preclude hydrolysis of the ester salt or will effect too slow a rate of hydrolysis. It has been found that an alkaline substance should be basic enough or present in sufficient amounts to provide a pH of at least about 10 in the solution.

Given the theoretical and experimental considerations of the present teachings, selection of the proper hydrolyzing agent can be routinely determined through conventional laboratory experimentation. All one skilled in the art need do to thus practice a preferred embodiment of the present invention is incorporate the ester salt, DMF and hydrolyzing agent in one or more carrier matrices as described herein, and then prepare a control solution. The generation of the desired $\beta$-keto acid occurs in situ and can be observed and followed by spectrophotometric or other analytical means known in the art. Insufficient generation of the keto acid is indicative of insufficient hydrolyzing agent, i.e., generation of a pH insufficient to hydrolyze substantially or rapidly the ester salt.

As stated supra, the ester salt of the present invention comprises one of a $\beta$-keto acid. In the structure of the ester salt depicted herein, where R is defined as being "lower alkyl", that term is meant to include alkyl groups having from 1 to 6 carbon atoms, including methyl, ethyl, n-butyl, sec-butyl, tert-butyl, isobutyl, cyclobutyl, and all pentyl and hexyl isomers. R', on the other hand, can taken on much broader significance. It can comprise an aliphatic group or a cyclic group having 1 to about 7 or more carbon atoms. These can be saturated, unsaturated, aromatic, substituted or unsubstituted. Especially suitable for the present invention are salts of such esters as methyl acetoacetate and ethylacetoacetate. Still others are ethyl 3-keto-4-phenylbutyrate, 1,10-di(acetoacetyl)decane, ethyl 2-methylacetoacetate, and ethyl p-fluorobenzoyl acetate. Salts of many additional $\beta$-keto esters are within the scope of the present invention, the only limiting requisites being that the ester salt is hydrolyzable in the presence of water to produce the corresponding $\beta$-keto acid.

The amount of $\beta$-keto ester salt utilized, i.e., in the composition of the invention which can be incorporated with a carrier matrix to form the control device, depends upon several parameters. First, the particular system in which ketone body presence might be of analytical interest demands an analytical system responsive to a certain range of ketone concentration. This concentration range will vary from system to system. Pathological urines, for example, necessitate that the ketone sensitive area of N-MULTISTIX reagent strips be responsive to ketone concentrations of from about 3 up to about 160 mg per dl (mg%). Accordingly, for a device for preparing a control solution for N-MULTIS- TIX reagent strips, an amount of ester salt sufficient to provide a color change indicative of ketone concentrations in that range is required.

A second determining factor is the volume of control solution the device will ultimately be used to prepare. Thus, if the device is incorporated with amounts of ingredients which when contacted with 30 milliliters of water will provide the desired N-MULTISTIX reagent strip response, that same device will provide too strong a response with 12 milliliters of water and too weak a response with one liter. It is important, therefore, that the amount of ester salt incorporated with the carrier vehicle be at least sufficient in a predetermined amount of solvent. In urinalysis procedures, that concentration range is typically from about 0.1 to about 160 millimoles per liter.

Although the Examples, infra, describe in detail the preparation of control devices according to the invention, a method for preparing such devices can be summarized as follows. Filter paper is impregnated with a composition comprising an organic solution or suspension of DMF and the $\beta$-keto ester salt. Thus, for example, a strip of filter paper is immersed in a solution of DMF and the sodium salt of methyl acetoacetate, and then dried. The proportion of DMF which is used in the composition is not critical, so long as it is sufficient, following drying of the impregnated strip, to enable some DMF to remain incorporated with the dried matrix on the strip, and is also a quantity sufficient to solubilize the ester salt used to an extent that the composition can be impregnated into the matrix. With the dried paper matrix thus incorporated with the active ingredients, it is attached to a rigid or semirigid support such as polystyrene film, for example, by use of a double-faced adhesive tape. In one procedure for making control devices of the invention, the impreganted paper is cut into narrow strips before mounting. The strips are then mounted on polystyrene film along one edge using the double-faced adhesive. The filter paper/polystyrene composite is then slit along lines perpendicular to the axis of the filter paper, thus providing an oblong polystyrene strip having a piece of impregnated filter paper at one end, the other end serving as a handle.

Incorporation of the composition of the invention with the carrier matrix can be accomplished in a variety of ways. In addition to the immersion procedure described supra, for example, the composition can be used to impregnate a filter paper pad by printing, as in the case of an ink, or the carrier matrix can be coated with the composition, such as with a doctor blade. A second filter paper pad, in a preferred embodiment, can be incorporated in the same manner, e.g., with a solution of a hydrolyzing agent, and affixed to the same polystyrene support strip in the manner previously described. In addition, for a multiple control device product, such as CHEK-STIX, the hydrolyzing agent can be incorporated with any such carrier matrix pad which contains substances which will not be deleteriously affected by the presence of the agent.

Since the loss on subsequent drying of the composition comprising the ester salt and DMF has been observed to the approximately 3% more than the normal loss on drying (approximately 2-3%) of such compounds when water has been used as a solvent in place of DMF, it is believed that a significant amount of DMR remains on the carrier matrix pad with the salt when the procedures to produce control devices of the invention are properly carried out. It is believed, therefore, that the unexpectedly enhanced stability of the composition and control test devices prepared in accordance with the present invention may be attributable to the formation of a complex between the ester salt and DMF in the composition.

A control test solution can be prepared from the instant composition by placing a device including it in a test tube filled with a predetermined volume of aqueous solution for a predetermined time. The control composition dissolves into the aqueous solution and the ester salt is hydrolyzed to the corresponding acid. The hydrolysis will take place spontaneously in water, but the rate of hydrolysis is increased, as previously described, by the presence of a base or other hydrolyzing agent, which produces a control solution having a pH of from about 10 to 11. A control test device of the invention can deliver a quantity of test composition which upon hydrolysis will provide a concentration of acid of from about 10 up to about 45 milligrams per deciliter, a range which can be determined visually using color comparison charts, or instrumentally, for example, using instruments such as CLINITEK® reflectance photometer, marketed by the Ames Division of Miles Laboratories. Inc.

The following examples describe experiments which were performed in developing the present invention and which illustrate presently preferred embodiments thereof. While the examples serve to thus illustrate the invention, they are in no way to be interpreted as limiting its scope, which is defined solely by the claims appended hereto.

EXAMPLE I

Eaton & Dikeman (E&D) 222 filter paper was impregnated with a control test composition of 5.0 grams (g) of sodium methylacetoacetate in 20.0 milliliters (ml) of dimethyl formamide, and dried in an oven at 90° C. for 25 minutes. A control test device was then prepared by laminating a 2/5 inch × 2.5 inch piece of the impregnated E&D 222 filter paper with double sided adhesive (DOUBLE STICK® from 3M Co.) and then applying it to a polystyrene strip (TRYCITE®, from Dow Chemical Co.). A control test solution was prepared by placing the device in a URINE-TEK® test tube filled to the 12.0 ml calibration mark with distilled water. The tube was inverted for about 2 minutes to completely immerse the device and allowed to stand for 30 minutes; the device was then removed.

A $\beta$-keto acid-specific test device, KETOSTIX®, marketed by Ames Division of Miles Laboratories, Inc., was dipped into the control test solution produced as described in the foregoing paragraph. The test device gave a positive response, indicative of its reactivity, which was confirmed by routine visual means (comparison with a standard color block chart). The reaction was observed to produce a color response corresponding to a concentration of about 40 milligrams per deciliter of $\beta$-keto acid (as acetoacetic acid) in the solution.

EXAMPLE II

A 2/5 inch × 2/5 inch piece of E&D 222 filter paper, which had been previously impregnated with 5.0 gm% $Na_2CO_3$ in water and dried, was laminated onto a device which had been prepared according to Example I, adjacent to the first carrier matrix. The procedure used was substantially identical to that described in Example I, and a control solution was prepared from the device as previously described in that Example. The solution was then tested in a manner similar to that described in Example I. The color response with a KETOSTIX strip was observed visually to be within the 40–80 milligram per deciliter color block range, when read immediately after preparation of the control solution, and also within that range when read 7 hours after its preparation, the device having been stored under ambient temperature (about 23° C.) for that period of time.

Control test compositions and devices were prepared according to the present invention substantially as described in Example II, and were subsequently subjected to heat stress testing at 60° C. and 50° C., in air for one and four week periods of time, respectively, in an oven. Subjecting a device to a heat stress test of 50° C. over a four week period was considered to correspond to a prolonged storage condition of about two years at ambient temperature (about 23° C.).

After the devices were heat stressed, control solutions were prepared from them and the solutions were tested against the KETOSTIX ketone test device for reactivity*. The results of the reactivity testing were recorded immediately after the control solutions were prepared, and after the control solutions had been maintained at ambient temperature (about 23° C.) for approximately 7 hours. The visual color readings of the test devices after reaction with the prepared control solutions were then assigned standard solution designations (SSD), which corresponded to the color chart available on the KETOSTIX commercial test label affixed to each bottle of this product. Each of the six color blocks was assigned a SSD number (0, 10, 20, 30, 40, 50), corresponding to the following concentrations of acetoacetic acid in the solution, respectively: negative, trace (5 mg/dl), small (15 mg/dl), moderate (40 mg/dl), large (80 mg/dl) and very large (160 mg/dl). In addition, identical control devices were produced and control solutions were prepared therefrom and heat stress tested as previously described, not in accordance with the present invention, but from control test compositions comprising 20.0 ml of water as the solvent, substituted for the DMF in the devices prepared pursuant to the invention. The results, expressed in SSD units, of the reactivity testing of the control solutions produced from the stressed devices according to the invention (using DMF), and from the stressed devices not in accordance therewith (using water), were visually obtained by reference to the color blocks. The results are presented in the following table, along with comparison data obtained from like control test devices which had not been subjected to heat stress.

*The control solutions were prepared substantially as described in the Examples, with the exception that the devices used were reconstituted without first immersing them in an inverted URINE-TEK ® tube for two minutes, as described therein; rather, they were immersed in 12.0 ml distilled water for 30 minutes.

SSD OF KETOSTIX ® REAGENT STRIP READINGS ON CONTROL SOLUTIONS PREPARED FROM UNSTRESSED AND STRESSED CONTROL TEST DEVICES

| Temperature and Storage Time of Device | Unstressed: Ambient temp. (23° C.) (0) | | Stressed: 60° C. (1 wk) | | Stressed: 50° C. (4 wks) | |
|---|---|---|---|---|---|---|
| Control Solution-(time at which readings taken following preparation-hours) | 0 | 7 | 0 | 7 | 0 | 7 |
| Control Test Device Composition | | | | | | |
| 25 g % sodium ethyl-acetoacetate in water | 21 | 29 | 6 | 9 | 0 | 4 |
| 25 g % sodium ethyl acetoacetate in DMF | 25 | 30 | 15 | 21 | 6 | 10 |
| 25 g % sodium methyl-acetoacetate in water | 22 | 26 | 29 | 32 | 0 | 0 |
| 25 g % sodium methyl-acetoacetate in DMF | 38 | 40 | 37 | 36 | 29 | 36 |

The tabulated data presented above demonstrates that control devices comprising compositions of the invention, i.e., those which included DMF, were superior in heat stress stability by comparison with compositions having the same ester salt but which included water in place of DMF. These results are illustrated by the greater concentrations of acetoacetic acid which the devices of the invention were able to produce in the control solutions. The MaMeAA and MDF composition, in particular, exhibited consistently good results, whether stressed or unstressed, producing control solutions containing concentrations of acetoacetic acid which were well within the range necessary to show a positive response with most standard ketone test devices which detect that compound.

Additional control solutions were prepared from control devices which had been produced according to the invention, using substantially the procedures described in Example II, supra, but which had remained in long-term storage under ambient temperature (about 23° C.) for slightly over three (3) years. The compositions used in these devices comprised DMF and either 25 g% sodium methylacetoacetate or 25 g% calcium methylacetoacetate. Unexpectedly, the SSD data produced from these control solutions appeared to be virtually unchanged from the SSD data obtained from control solutions prepared from substantially the same control devices but immediately after they had been made. These results were believed to indicate that the β-keto ester salt combination with DMF of the composition of the instant invention functions to stabilize the reactivity of such control devices, even after greatly prolonged storage, enabling an especially advantageous, lengthy shelf life for the devices.

What is claimed is:

1. A stable composition useful for preparing a ketone control solution, said composition comprising dimethylformamide and a predetermined quantity of a β-keto ester salt capable of being hydrolyzed in aqueous solution to a β-keto acid and having the formula $$\left[ R'-\underset{\underset{O}{\|}}{C}=CH-\underset{\underset{O}{\|}}{C}-OR \right]_n M^{n+}$$

in which R is lower alkyl of 1 to 6 carbon atoms, R' is an aliphatic group having 1 to 7 carbon atoms or cyclic group, M is a Group I, II or III metal ion and n is 1, 2 or 3.

2. The composition of claim 1 wherein R' is an aliphatic group having 1 to 7 carbon atoms.

3. The composition of claim 1 wherein R' is methyl.

4. The composition of claim 1 wherein the β-keto ester salt is sodium methylacetoacetate.

5. The composition of claim 1 wherein the β-keto ester salt is sodium ethylacetoacetate.

6. The composition of claim 1 wherein the β-keto ester salt is calcium methyl acetoacetate.

7. A device useful in the preparation of a ketone control solution, said device comprising
a carrier matrix incorporated with the composition of any one of claims 1 through 6; and
a support member having said carrier matrix affixed thereto.

8. A device useful in the preparation of a ketone control solution, said device comprising
a carrier matrix incorporated with the composition of any one of claims 1 through 6 and a hydrolyzing agent; and
a support member having said carrier matrix affixed thereto.

9. A device useful in the preparation of a ketone control solution, said device comprising
a carrier matrix incorporated with the composition of any one of claims 1 through 6;
a second carrier matrix incorporated with a hydrolyzing agent; and
a support member having each of said carrier matrices affixed thereto.

10. The device of claim 8 wherein the hydrolyzing agent is a base.

11. The device of claim 9 wherein the hydrolyzing agent is a base.

12. The device of claim 10 wherein the hydrolyzing agent is selected from the group consisting of sodium carbonate, potassium carbonate, sodium hydroxide, potassium hydroxide and mixtures thereof.

13. The device of claim 10 wherein the hydrolyzing agent is sodium carbonate.

14. The device of claim 11 wherein the hydrolyzing agent is selected from the group consisting of sodium carbonate, potassium carbonate, sodium hydroxide potassium hydroxide and mixtures thereof.

15. The device of claim 11 wherein the hydrolyzing agent is sodium carbonate.

16. A method for preparing a ketone control solution, which method comprises contacting a predetermined volume of an aqueous solution with the device of claim 7 for a predetermined time, and thereafter removing said device from contact with the solution.

17. A method for preparing a ketone control solution, which method comprises contacting a predetermined volume of an aqueous solution with the device of claim 8 for a predetermined time, and thereafter removing said device from contact with the solution.

18. A method for preparing a ketone control solution, which method comprises contacting a predetermined volume of an aqueous solution with the device of claim 9 for a predetermined time, and thereafter removing said device from contact with the solution.

* * * * *